US00PP11946P2

(12) United States Plant Patent
Booman

(10) Patent No.: US PP11,946 P2
(45) Date of Patent: Jun. 19, 2001

(54) BEGONIA PLANT NAMED 'SEATTLE TWIST'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,789

(22) Filed: Aug. 17, 1999

(51) Int. Cl.[7] ..... A01H 5/00

(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Seattle Twist', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Seattle Twist'.

The new Rex Begonia was discovered by the Inventor in a controlled environment in Vista, Calif., in August, 1996, as a naturally-occurring mutation of *Begonia rex* hybrid 'Lalome', not patented. The new Rex Begonia was observed as a single plant in a group of plants of the parent cultivar. The selection of this plant was based on its unique leaf coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Seattle Twist' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Seattle Twist'. These characteristics in combination distinguish 'Seattle Twist' as a new and distinct Rex Begonia:

1. Uniform growth habit.
2. Moderate plant vigor.
3. Does not require winter dormancy.
4. Stable, interesting and attractive leaf coloration, pattern and texture.
5. Partial "corkscrew" leaf formation.

Compared to plants of the parent cultivar Lalome, zonation patterns on leaves of the new Rex Begonia are more distinct and stable.

In side-by-side comparisons conducted by the Inventor in Vista, Calif., plants of the new Rex Begonia differ from plants of the nonpatented cultivar 'Merry Christmas Corkscrew' in the following characteristics:

1. Plants of the new Rex Begonia grow more rapidly than plants of the cultivar 'Merry Christmas Corkscrew'.

2. Plants of the new Rex Begonia have larger and flatter leaves than plants of the cultivar 'Merry Christmas Corkscrew'.
3. Leaves of plants of the new Rex Begonia have a less pronounced "corkscrew" formation than leaves of plants of the cultivar 'Merry Christmas Corkscrew'.
4. Plants of the new Rex Begonia do not require a winter dormancy period whereas plants of the cultivar Merry Christmas Corkscrew do require a winter dormancy period.

In side-by-side comparisons conducted by the Inventor in Vista, Calif., plants of the new Rex Begonia differ from plants of the nonpatented cultivar Lillium in the following characteristics:

1. Plants of the new Rex Begonia have larger and flatter leaves than plants of the cultivar Lillium.
2. Leaves of plants of the new Rex Begonia have a "corkscrew" formation whereas leaves of plants of the cultivar Lillium do not have a "corkscrew" formation.
3. Plants of the new Rex Begonia do not require a winter dormancy period whereas plants of the cultivar Lillium do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Seattle Twist'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar 'Seattle Twist'.

Commercial classification: Rex Begonia.

Parentage: Naturally-occurring mutation of *Begonia rex* hybrid 'Lalome', not patented.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 28.5 cm.

*Plant width.*—About 56 cm.

*Leaves.*—Arrangement: Simple. Length: Petiole to apex: About 19 cm. Base to apex: About 28 cm. Width: About 22 cm. Shape: Obliquely ovate to rounded; partial "corkscrew" formation. Apex: Acute. Base: Unevenly cordate and overlapping, partial "corkscrew" formation. Margin: Pectinate; irregularly undulate. Texture: Leathery, rugose; pubescence on lower surface veins. Color: Young foliage, upper surface: Margin: 187A with antemarginal border of 186C. Central venal areas: 200C, bordered by metallic 186B to 186C, with overtones of 185B. Blade: Iridescent, 148D and 194C, with a background of 146A. Speckles of 148D and 194C extending to margin. Young foliage, lower surface: Margin: 187B. Central venal areas: 178A, bleeding along veins. Background: 148C. Mature, fully expanded, foliage, upper surface: Margin: Dark brown, 200A, with spots of 187C. Central venal areas: 200A, close to 202A. Blade: Iridescent, 194A to 194B, with blush of iridescent 186A to 186C bordering central venal area. Antemarginal: Splotches, close to 147A. Veins: 200C. Mature, fully expanded, foliage, lower surface: Margin: 200A. Central venal area: 183A. Background: 147C to 148C. Veins: Darker than 183A; reticulate.

*Petioles.*—Length: About 18.7 cm. Diameter: About 10 mm. Shape: Longitudinally grooved. Texture: Pubescent. Color: 183A.

*Stipules.*—Length: About 2.5 cm. Diameter at base: About 1.25 cm. Shape: Subulate, deltoid. Color: 46A, translucent.

Flower description:

*Flowering habit.*—Male flowers, single with one whorl of four tepals. Female flowers, semi-double with three tepals inerior to outer whorl of five tepals. Usually about five flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 3.4 cm. Depth (height): About 2.7 cm. Aspect: Drooping about 40° from vertical. Fragrance: None.

*Flower buds.*—Shape: Ovoid; bulbous with marginal lip. Length: About 1.6 cm. Diameter: About 1.4 cm. Color: 180A to 181D towards apex.

*Tepals.*—Arrangement: Rosette. Length: About 1.7 cm. Width: About 1.7 cm. Shape: Ovate with obtuse apex. Margin: Entire. Texture: Smooth, waxy; iridescent, translucent. Color: When opening, upper surface: 55B. When opening, lower surface: 52C to 55B. Fully opened, upper surface: 55B. Fully opened, lower surface: 52C to 55B.

*Peduncles.*—Angle: About 30° from vertical. Length: About 10 cm. Diameter: About 3.5 mm. Strength: Firm. Texture: Smooth, waxy. Color: 183A.

*Pedicels.*—Angle: About 45° from vertical. Length: About 1.9 cm. Diameter: About 2.5 mm. Strength: Moderate. Texture: Smooth, waxy. Color: 178B to 178C.

*Reproductive organs.*—Male flowers: Stamen quantity: About 120, globose mass. Anther shape: Rhomboidal; lower sides curved inwardly. Anther length: About 3 mm. Filament length: About 2 mm. Anther color: Close to 12C. Pollen: Not observed. Female flowers: Pistil length: About 1.7 cm. Stigma shape: Funnel; bilobate. Stigma color: 25A. Ovary: Inferior; three-winged; one large top wing, and two lower wings; both surfaces, 34A.

Disease resistance: Resistance to diseases common to Rex Begonia has not been determined.

Seed production: Seed production has not been observed.

It is claimed:

1. A new and distinct cultivar of Rex Begonia plant named 'Seattle Twist', as illustrated and described.

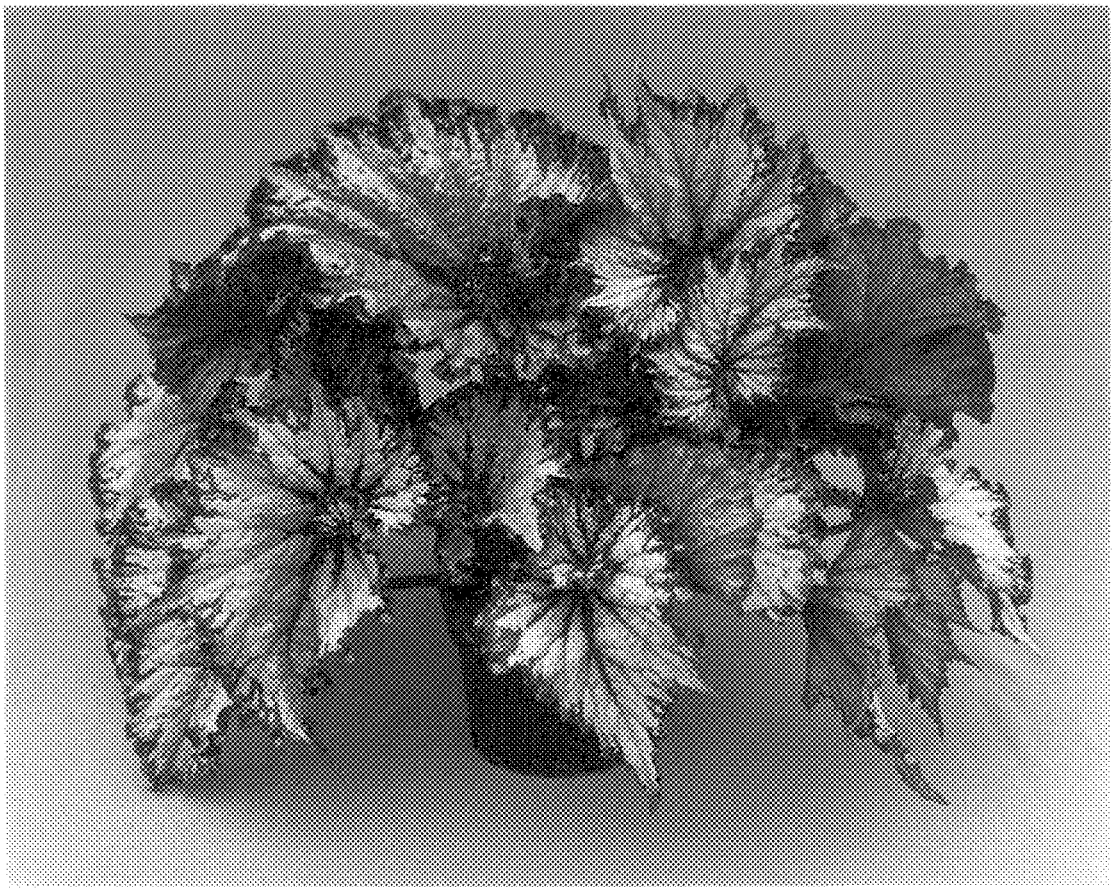

* * * * *